United States Patent [19]

Barcza

[11] Patent Number: 4,528,191
[45] Date of Patent: Jul. 9, 1985

[54] DISILACYCLOHEXANE DERIVATIVES IN ANTI-FERTILITY AGENTS

[75] Inventor: Sandor Barcza, Mt. Lakes, N.J.

[73] Assignee: Sandoz, Inc., East Hanover, N.J.

[21] Appl. No.: 577,523

[22] Filed: Feb. 6, 1984

Related U.S. Application Data

[63] Continuation-in-part of Ser. No. 545,060, Oct. 25, 1983, abandoned.

[51] Int. Cl.³ .................................... A61K 31/695
[52] U.S. Cl. ............................................. 514/63
[58] Field of Search ................................ 424/184

[56] References Cited

U.S. PATENT DOCUMENTS 4,208,408  6/1980  Barcza .................... 424/184

Primary Examiner—Leonard Schenkman
Attorney, Agent, or Firm—Gerald D. Sharkin; Robert S. Honor; Thomas O. McGovern

[57] ABSTRACT

This disclosure relates to the aspermatogenesis activity of compounds of the following formula:

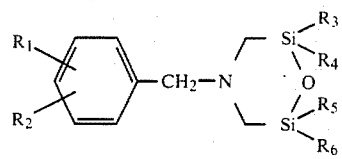

where
$R_1$ and $R_2$ each independently represent hydrogen, halo having an atomic weight of about 19 to 36, lower alkyl having 1 to 4 carbon atoms, lower alkoxy having 1 to 4 carbon atoms, trifluoromethyl, or
$R_1$ is

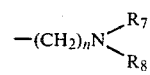

and $R_2$ is hydrogen,
wherein
$R_7$ and $R_8$ are each independently hydrogen or lower alkyl having 1 to 2 carbon atoms,
n is 0 or 1, and
$R_3$, $R_4$, $R_5$ and $R_6$ each independently represent lower alkyl having 1 to 2 carbon atoms or
a pharmaceutically acceptable salt thereof.

7 Claims, No Drawings

DISILACYCLOHEXANE DERIVATIVES IN ANTI-FERTILITY AGENTS

This is a continuation in part of U.S. patent application Ser. No. 545,060 filed Oct. 25, 1983 now abandoned.

This invention relates to the aspermatogenesis activity of disilacycyclohexane derivatives. More particularly, this invention concerns the use of 4-benzyl derivatives of 1-oxa-4-aza-2,6-disilacycyclohexanes as male anti-fertility agents.

The active agents with which this invention is concerned may be represented by the following structural formula:

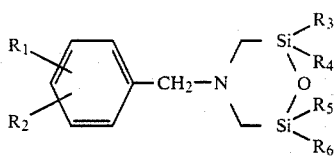

where
$R_1$ and $R_2$ each independently represent hydrogen, halo having an atomic weight of about 19 to 36, lower alkyl having 1 to 4 carbon atoms, lower alkoxy having 1 to 4 carbon atoms, trifluoromethyl, or
$R_1$ is

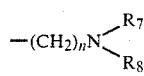

and
$R_2$ is hydrogen,
wherein
$R_7$ and $R_8$ are each independently hydrogen or lower alkyl having 1 to 2 carbon atoms,
n is 0 or 1, and
$R_3$, $R_4$, $R_5$ and $R_6$ each independently represent lower alkyl having 1 to 2 carbon atoms or
a pharmaceutically acceptable salt thereof.

The preferred compound is 4-(m-methoxybenzyl)-2,2,6,6-tetramethyl-1-oxa-4-aza-2,6-disilacycyclohexane. This compound and the above compounds of formula (I) are known and can be prepared by methods disclosed in U.S. Pat. No. 4,208,408.

The compounds of formula (I) may be administered as such or in the form of their non-toxic pharmaceutically acceptable acid addition salts. Such salts possess the same order of activity as the free base and are readily prepared by reacting the compound with a pharmaceutically acceptable acid by conventional techniques. Representative of the inorganic salts are the hydrochloride, hydrobromide, hydroiodide, phosphate (including hydrogen phosphate), metaphosphate, and sulfate (including hydrogen sulfate). Representative examples of the organic salts are the acetate, maleate, fumarate and the like. The use of such salt forms as male anti-fertility agents also form part of the invention.

As disclosed above, the compounds of formula (I) are useful because they possess aspermatogenesis activity in mammals. In particular, the compounds of formula (I) are useful as male anti-fertility agents, as indicated by the reduction or cessation of spermatogenic activity in adult Beagle dogs. Adult Beagle dogs in groups of two are given orally 12, 36 and 120 milligrams per kilograms per day (mg/kg/day) of the test compound for 14 to 16 consecutive days. Semen samples are collected from all dogs one week before testing is commenced and weekly thereafter to determine microscopically the sperm counts essentially in accordance with the procedure of Kolmer, et al (Approved Laboratory Technique, 5th Ed., (286, 1959). Upon necropsy, the dogs are sacrificed; and the testes and epididymis from all animals are collected and preserved in 10% neutral buffered formalin until examined histopathologically for various stages of aspermatogenesis.

In an alternate test method, young adult male Beagle dogs in groups of three are given orally 10, 30, and 120 mg/kg/day of test compound. One group is given the drug for one week and then sacrificed. A second group used as control and a third group given the drug are sacrificed after four weeks. A fourth group is given the drug for four weeks, and then is sacrificed after eighteen weeks without drug to determine reversibility of the drug induced aspermatogenesis. Clinical observations are performed daily and body weights are taken weekly. Complete necropsies are performed and both testes from all dogs are examined histologically for various stages of aspermatogenesis.

When the above tests are carried out with 4-(m-methoxybenzyl)-2,2,6,6-tetramethyl-1-oxa-4-aza-2,6-disilacycyclohexane, aspermatogenesis is observed in the dogs. After administration of the drug is stopped, sperm count returns to normal; and upon necropsy, histopathological examination reveals no evidence of testicular damage or aspermatogenesis.

When the alternate test is carried out with 60 mg/kg/day of the above 4-(m-methoxybenzyl)-2,2,6,6-tetramethyl-1-oxa-4-aza-2,6-disilacycyclohexane, spermatogenesis is greatly reduced or totally absent in all three dogs examined after the first week. At the end of four weeks, spermatogenesis is totally absent in the dogs given the compound, and normal for the dogs in the control group. Spermatogenesis and testicular histology is essentially normal in the dogs given the compound for four weeks and then examined eighteen weeks after administration of the compound is stopped.

For use as anti-fertility agents, the compounds of formula (I) and their non-toxic, pharmaceutically acceptable salts may be administered orally as such or orally and parenterally with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., magnesium stearate, stearic acid and talc. The tablets may be coated by known techniques to delay disintegration and absorption in the gastro-intestinal tract and thereby provide a sustained action over a longer period. Similarly, suspension, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated by methods well known in the art. These pharmaceutical preparations contain from about 0.5 to about 90 percent by weight based on the final composition of the active ingredient in combination with the carrier or adjuvant.

The anti-fertility effective dosage of the compounds of formula (I) employed in producing aspermatogenesis will vary depending on the particular compound employed. In general, satisfactory results are obtained when the compounds of formula (I) are administered at a daily dosage of from about 12 milligrams to about 120 milligrams per kilogram of animal body weight, preferably given in divided doses one or two times a day, or in sustained release form. For most large mammals, the total daily dosage is from about 200 to about 2000 milligrams, preferably 500 to about 1000 milligrams. Dosage forms suitable for internal use comprise from about 100 to about 1000 milligrams of the active compound in intimate admixture with a solid or liquid pharmaceutically acceptable carrier or diluent.

The preferred pharmaceutical compositions from the standpoint of preparation and ease of administration are solid compositions, particularly hard-filled capsules and tablets containing from about 250 to about 500 milligrams of the active ingredient.

TABLETS AND CAPSULES SUITABLE FOR ORAL ADMINISTRATION

Tablets and capsules containing the ingredients indicated below may be prepared by conventional techniques and are useful as an anti-fertility agent at a dose of one or two tablets or capsules two to four times a day.

| Ingredients | Weight (mg.) tablet | Capsule |
|---|---|---|
| 4-(m-methoxybenzyl)-2,2,6,6-tetramethyl-1-oxa-4-aza-2,6-disilacyclohexane | 250 | 250 |
| Tragacanth | 10 | — |
| Lactose | 197.5 | 250 |
| Corn Starch | 25 | — |
| Talcum | 15 | — |
| Magnesium Stearate | 2.5 | — |
| Total | 500 | 500 |

Similar results are obtained when the above disilacycyclohexane active agent is replaced by
(a) 4-(p-chlorobenzyl)-2,2,6,6-tetramethyl-1-oxa-4-aza-2,6-disilacyclohexane,
(b) 4-(p-fluorobenzyl)-2,2,6,6-tetramethyl-1-oxa-4-aza-2,6-disilacyclohexane,
(c) 4-(p-methylbenzyl)-2,2,6,6-tetramethyl-1-oxa-4aza-2,6-disilacyclohexane,
(d) 4-(p-methoxybenzyl)-2,2,6,6-tetramethyl-1-oxa-4-aza-2,6-disilacyclohexane,
(e) 4-(3,4-dichlorobenzyl)-2,2,6,6-tetramethyl-1-oxa-4-aza-2,6-disilacyclohexane,
(f) 4-(3-trifluoromethylbenzyl)-2,2,6,6-tetramethyl-1-oxa-4-aza-2,6-disilacyclohexane,
(g) 4-(4-dimethylaminobenzyl)-2,2,6,6-tetramethyl-1-oxa-4-aza-2,6-disilacyclohexane,
(h) 4-(4-dimethylaminomethylbenzyl)-2,2,6,6-tetramethyl-1-oxa-4-aza-2,6-disilacyclohexane,
(i) 4-(m-chlorobenzyl)-2,2,6,6-tetramethyl-1-oxa-4-aza-2,6-disilacyclohexane,
(j) 4-(m-methylbenzyl)-2,2,6,6-tetramethyl-1-oxa-4-aza-2,6-disilacyclohexane, or
(k) 4-(o-chlorobenzyl)-2,2,6,6-tetramethyl-1-oxa-4-aza-2,6-disilacycyclohexane,
or a pharmaceutically acceptable acid addition salt thereof.

What is claimed is:
1. A method of inducing aspermatogenesis in male mammals in need of anti-fertility treatment which comprises administering to the mammal an anti-fertility effective amount of a compound of the formula:

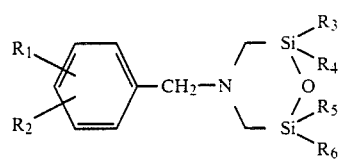

where
$R_1$ and $R_2$ each independently represent hydrogen, halo having an atomic weight of about 19 to 36, lower alkyl having 1 to 4 carbon atoms, lower alkoxy having 1 to 4 carbon atoms, trifluoromethyl, or
$R_1$ is

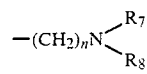

and
$R_2$ is hydrogen,
wherein
$R_7$ and $R_8$ are each independently hydrogen or lower alkyl having 1 to 2 carbon atoms,
n is 0 or 1, and
$R_3$, $R_4$, $R_5$ and $R_6$ each independently represent lower alkyl having 1 to 2 carbon atoms or
a pharmaceutically acceptable salt thereof.

2. A method according to claim 1 in which 200 to 2000 milligrams of the compound are administered daily.

3. A method according to claim 1 in which 500 to 1000 milligrams of the compound are administered daily.

4. A method according to claim 1 in which 100 to 1000 milligrams of the compound are administered per unit dose.

5. A method according to claim 1 in which 250 to 500 milligrams of the compound are administered per unit dose.

6. The method according to claim 1 in which the compound is 4-(m-methoxybenzyl)-2,2,6,6-tetramethyl-1-oxa-4-aza-2,6-disilacycyclohexane or a pharmaceutically acceptable acid addition salt thereof.

7. The method according to claim 1 in which the compound is
(a) 4-(p-chlorobenzyl)-2,2,6,6-tetramethyl-1-oxa-4-aza-2,6-disilacycyclohexane,
(b) 4-(p-fluorobenzyl)-2,2,6,6-tetramethyl-1-oxa-4-aza-2,6-disilacycyclohexane,
(c) 4-(p-methylbenzyl)-2,2,6,6-tetramethyl-1-oxa-4-aza-2,6-disilacycyclohexane, (d) 4-(p-methoxybenzyl)-2,2,6,6-tetramethyl-1-oxa-4-aza-2,6-disilacycyclohexane,
(e) 4-(3,4-dichlorobenzyl)-2,2,6,6-tetramethyl-1-oxa-4-aza-2,6-disilacycyclohexane,
(f) 4-(3-trifluoromethylbenzyl)-2,2,6,6-tetramethyl-1-oxa-4-aza-2,6-disilacycyclohexane,
(g) 4-(4-dimethylaminobenzyl)-2,2,6,6-tetramethyl-1-oxa-4-aza-2,6-disilacycyclohexane,
(h) 4-(4-dimethylaminomethylbenzyl)-2,2,6,6-tetramethyl-1-oxa-4-aza-2,6-disilacycyclohexane,
(i) 4-(m-chlorobenzyl)-2,2,6,6-tetramethyl-1-oxa-4-aza-2,6-disilacycyclohexane,
(j) 4-(m-methylbenzyl)-2,2,6,6-tetramethyl-1-oxa-4-aza-2,6-disilacycyclohexane,
(k) 4-(o-chlorobenzyl)-2,2,6,6-tetramethyl-1-oxa-4-aza-2,6-disilacycyclohexane, or a pharmaceutically acceptable acid addition salt thereof.

* * * * *